United States Patent [19]

Walt et al.

[11] Patent Number: 4,920,958
[45] Date of Patent: May 1, 1990

[54] DRILL GUIDE ASSEMBLY

[75] Inventors: Michael J. Walt, North St. Paul; Craig L. Van Kampen, Oakdale; Steven J. May, Minnetonka, all of Minn.

[73] Assignee: Minnesota Mining and Manufacturing Company, St. Paul, Minn.

[21] Appl. No.: 214,916

[22] Filed: Jun. 27, 1988

Related U.S. Application Data

[63] Continuation of Ser. No. 927,128, Nov. 5, 1986, abandoned.

[51] Int. Cl.$^5$ .................... A61F 5/04; A61F 17/32
[52] U.S. Cl. ........................................ 606/96; 606/103
[58] Field of Search ....... 128/92 VD, 92 VK, 92 VL, 128/92 VW, 92 V, 92 R, 305.1

[56] References Cited

U.S. PATENT DOCUMENTS

| 4,535,768 | 8/1985 | Hourahane et al. | 128/92 VD |
| 4,672,957 | 6/1987 | Hourahane | 128/92 VD |

FOREIGN PATENT DOCUMENTS

| 2147504 | 5/1985 | United Kingdom | 128/92 VD |

OTHER PUBLICATIONS

Arthrex Catalog, Norwalk, Connecticut.
Variable Radius-VR Drill Guide Norwalk, Connecticut.
Bow and Arrow-Makar, Inc., Okemos, Michigan.
O.S.I. Isometric ACL Reconstruction System-Hayard, California.
Nisonson Wire and Drill Guide System sold by: Stryker-Kalamazoo, Michigan.
Richards Arthroscopic Ligament Drill Guide sold by: Richards Medical Company-Memphis, Tennessee.
Techmedica Ligament Installation System (L.I.S.) sold by: Techmedica-Camarillo, California.
Vector Guide to the Knee System sold by: Dyonics, Inc.-Andover, Massachusetts.
Bow and Arrow sold by: Instrument Makar, Inc.-Okemos, Michigan.
Arthrex Arthroscopic ALC Replacement Drill Guide sold by: Arthrex Arthroscopy-Instruments, Inc., Norwalk, Connecticut.
Variable Radius*-VR Drill Guide sold by: Arthrex Arthroscopy Instruments, Inc., Norwalk, Connecticut.
OSI Isometric ACL Reconstruction System sold by: Orthopedic Systems, Inc.-Hayward, California.
Hendler's Uni-Tunnel Drill Guide sold by: Richard Wolf Medical Instruments Corp., Rosemont, Illinois.
Lipscomb Anderson Drill Guide sold by: Richards Medical Company-Memphis, Tennessee.
Anterior Cruciate Drill Guide & Posterior Cruciate Drill Guide sold by: A. W. Showell (Surgicraft) Ltd., Britten St. Redditch, Worcestershire, England.
Protek Drill Guide sold by: Protec AG-Indianapolis, Indiana.
Acufex Arthroscopic Drill System sold by: Acufex Microsurgical, Inc.-Norwood, Ma.
Newson Ligament Drill Guide sold by: Richards Manufacturing Co., Inc.-Memphis, Tennessee.
Stille Drill Guide sold by: Depuy-Warsay, Indiana.

Primary Examiner—Mickey Yu
Assistant Examiner—Michael Brown
Attorney, Agent, or Firm—Donald M. Sell; Walter N. Kirn; Stephen W. Bauer

[57] ABSTRACT

A drill guide assembly for use in arthroscopic surgery including a probe having a target end and an opposite threaded end portion with a locating lug; a cannular elongate wire guide adapted to guide a guide wire, which wire guide has a beveled bone contact end surface; a body generally arcuate about a predetermined point having a bore adapted to receive the wire guide for longitudinal sliding action with its axis aligned with the predetermined point, and a second end portion with a plurality of sockets adapted to releasably receive the lug and threaded end portion with the target end at the predetermined point; and a locking spring for preventing movement of the wire guide away from the predetermined point.

10 Claims, 2 Drawing Sheets

DRILL GUIDE ASSEMBLY

This is a continuation of application Ser. No. 927,128 filed Nov. 5, 1986, abandoned.

TECHNICAL FIELD

The present invention relates to drill guide assemblies adapted to help insert a wire into a bone at a predetermined position, which wire, after insertion, will provide a guide for a cannulated drill by which a passageway is then formed in the bone.

BACKGROUND ART

Many drill guide assemblies are known by which a wire may be inserted into a bone at a predetermined position, which wire, after insertion, will provide a guide for a cannulated drill driven by a drill motor by which a passageway can then be formed in the bone to afford such procedures as ligament replacement. Typical examples of such drill guide assemblies are The Nisonson Wire and Drill System sold by Stryker, Kalamazoo, MI; The Richards Arthroscopic Ligament Drill Guide Set sold by Richards Medical Company, Memphis, TN; the Techmedica Ligament Installation System sold by Techmedica, Camarillo, CA; The Vector Guide to the Knee System, sold by Dyonics, Inc. Andover, ME; The Bow and Arrow sold by Instrument Maker, Inc., Okemos, MI; The Arthroscopic Drill Guide Set sold by Arthrex Arthroscopy Instruments, Inc., Norwalk, CT; and the Variable Radius Drill Guide System sold by Arthrex Arthroscopy Instruments, Norwalk, CT.

Of these assemblies, the last three have the closest structures to the structure of the present invention in that they both include (1) a probe having a target end and an opposite threaded end portion, (2) a cannular elongate cylindrical wire guide having a central through opening adapted to receive and guide a wire, (3) a body generally arcuate about a predetermined point, having a first end portion with a through bore adapted to closely receive the wire guide for longitudinal sliding action with the axis of the wire guide aligned with the predetermined point, and having a second end portion adapted to receive the threaded end portion of the probe with the target end at the predetermined position and a part of the threaded end portion accessible from the side of the body opposite the predetermined point on which an attaching member is engaged to secure the probe on the body, and (4) means for preventing longitudinal movement of the wire guide through the bore away from the predetermined point.

These last three prior art drill guides have several structural deficiencies, however, which are as follows:

(1) The body of each has a cross section that is elongate in a direction at a right angle to the axes of the probe and wire guide. Thus, the portion of the body available to accurately anchor and align the probe and wire guide is relatively thin, and forces tending to deflect the distal ends of the probe and wire guide can more easily bend the body than might otherwise be the case.

Also, in the last two of these prior art drill guide assemblies, the second end portion of the body in which the probe is fixed is slotted, which, while providing a wide range of adjustments for the angle of the probe with respect to the drill guide, does not provide sufficiently precise support for the threaded end portion of the probe so that the target end of the probe will always be positioned with the accuracy that is desired.

(2) The end surfaces of the wire guides that are intended to contact a bone into which the wire is to be inserted are disposed generally at right angles to the axes of the wire guides. Thus, when a wire is inserted into a bone at an angle to the surface of the bone (which is quite often done, typically at an angle of about 45 degrees or less between the surface of the bone and the axis of the wire guide), only an edge (which edge may be toothed to help retain its position on the bone) of the wire guide contacts the bone and when the wire is inserted into the bone the tip of the wire is not supported between the end surface of the wire guide and the surface of the bone on the side of the wire guide toward which the end of the wire can be deflected by contact with the relatively hard surface of the bone. This unsupported distance is significant because of the angle of about 45 degrees or more that also typically exists between the end surface of the wire guide and the surface of the bone. If the thus unsupported end of the wire strikes and is deflected by the outer surface of the bone, it will enter the bone at the wrong place and thus will not be inserted along its intended path. In some drill guide assemblies this unsupported space is minimized in that the end of the drill guide adapted to contact the bone is tapered to a thin edge. Such thin edges tend to bend or dull with use, however, so that accurate positioning of that end becomes difficult. Other drill guide assemblies have wider and thus stronger end surfaces, however, the width of such an end surface increases the unsupported distance described above.

(3) The means for preventing longitudinal movement of the wire guide through the bore away from the predetermined point is a manually operated set screw which can be difficult to tighten during an operation while maintaining a desired relative position between the body and wire guide.

DISCLOSURE OF INVENTION

The present invention provides a drill guide assembly of the type indicated above for use in arthroscopic surgery in which the relationship between a body and a probe is more positively established so that the target end of the probe will more reliably be positioned at a predetermined position defined by the assembly, which provides support for the wire to a position more closely adjacent the surface of the bone so that the wire can more reliably be inserted along its intended part through the bone, and which provides means for preventing longitudinal movement of the wire guide away from the predetermined point that does not require manual tightening after the wire guide and body are positioned in their desired relative locations.

The drill guide assembly according to the present invention for use in arthroscopic surgery comprises (1) a probe having a target end, an opposite threaded end portion and a locating lug at the end of the threads adjacent the target end; (2) a cannular elongate cylindrical wire guide having a central through opening adapted to receive and guide a guide wire, and a single beveled end surface adapted to contact a bone; (3) a body generally arcuate about a predetermined point and having a cross sectional area that is elongate in a radial direction from the predetermined point, the body having a first end portion with a through bore adapted to closely receive the wire guide for longitudinal sliding action with the axis of the wire guide aligned with the predetermined point, and having a second end portion having a plurality of sockets extending through the body, each of which sockets is adapted to receive the threaded end portion and lug of the probe with its target end at the predetermined position and a part of the threaded end portion accessible from the side of the body opposite the predetermined point; (4) an attaching member adapted to engage the part of the threaded end portion on the side of the body opposite the predetermined point when the probe is engaged in one of the sockets; and (5) means for preventing longitudinal movement of the wire guide through the bore away from the predetermined point, while affording movement of the wire guide toward the predetermined point.

The elongate cross sectional area of the body in a radial direction from the predetermined point both insures that the body cannot easily be bent by forces applied at the distal ends of the probe and wire guide, and provides substantial engagement between the body and the probe and wire guide so that their distal ends can be accurately located.

Preferably the beveled end surface is disposed at an angle of about 25 degrees with respect to the axis of the wire guide so that with the axis of the wire guide disposed at a typical 45 degree angle with respect to the surface of a bone in which the wire is to be inserted and the contact end surface disposed so that it forms the minimum possible angle (i.e., about 20 degrees) with respect to the surface of the bone, the end of a wire inserted through the wire guide and into the bone will be unsupported for only a very short distance which will restrict the wire from deflecting out of its intended path when it engages the side of the bone. Also, the pointed tip of the wire guide defined by its side and contact end surfaces can be easily engaged with the bone by impacting the wire guide with a hammer to help retain the position of the wire guide with respect to the bone, and further reduce the space between the bone and the adjacent contact end surface of the wire guide.

Also, preferably the wire guide has marks along its length indicating, by their locations relative to the body, the distance between the contact end surface of the wire guide and the predetermined point, which is useful for the surgeon in determining the length of the wire path through the bone.

Preferably, the means for preventing movement of the wire guide away from the predetermined point comprises a U-shaped spring including one portion attached to the body on its sides opposite the predetermined point, and a cantilevered portion on the side of the attached portion opposite the body. The spring has openings through both portions, which openings are generally aligned with the bore and of sufficient diameter to afford longitudinal sliding movement of the wire guide through the openings and bore when the cantilevered portion of the spring is deflected toward said body, (which deflection will occur when the wire guide is moved toward the predetermined point), while the opening in the cantilevered portion will move out of alignment with the bore when the cantilevered portion moves to its normal position (which will happen when the wire guide is stationary or is biased to move away from the predetermined point) so that the edges of the cantilevered portion defining the opening therein engage the wire guide to prevent movement of the wire guide away from the predetermined point.

BRIEF DESCRIPTION OF THE DRAWING

The present invention will be further described with reference to the accompanying drawing wherein like numbers refer to like parts in the several views, and wherein.

DETAILED DESCRIPTION

Figure 1:
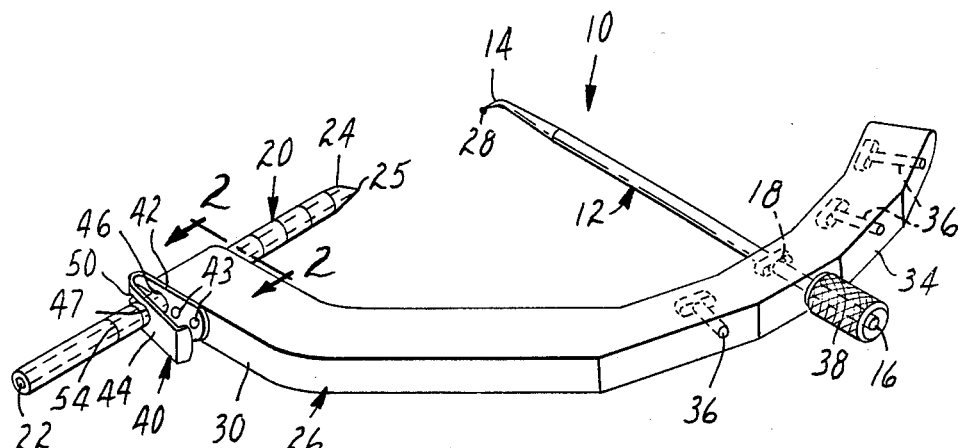
FIG. 1 is a view in perspective of a drill guide assembly according to the present invention.
Figure 2:
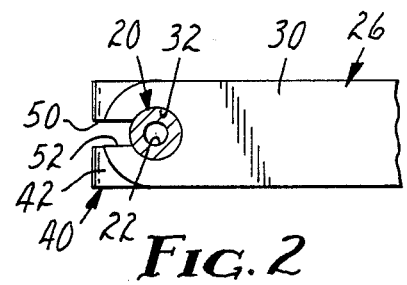
FIG. 2 is a fragmentary enlarged sectional view taken approximately along line 2—2 of FIG. 1.
Figure 3:
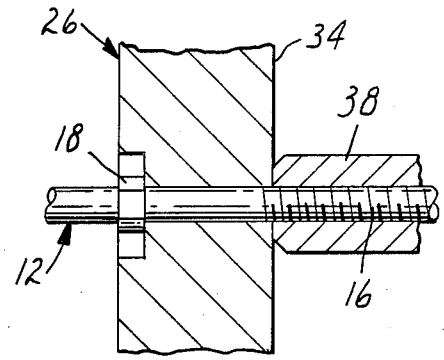
FIG. 3 is an enlarged fragmentary sectional view showing engagement of a probe with a body of the drill guide assembly shown in FIG. 1.

Referring now to the drawing there is shown a drill guide assembly for use in arthroscopic surgery generally designated by the reference numeral 10.

The drill guide assembly 10 comprises a stainless steel probe 12 having a pointed target end 14 bent at about a right angle (e.g., 82.5 degrees) to the major portion of the probe 12, an opposite threaded end portion 16 and a locating lug 18 which is generally rectangular with rounded ends located at the end of the threaded end portion 16 adjacent the target end 14.

Also included is a cannular elongate cylindrical hardened stainless steel (e.g., Rockwell C38) wire guide 20 having a central through opening 22 adapted to receive and guide a guide wire, and a single beveled end surface 24 disposed at an angle of about 25 degrees with respect to the axis of the wire guide 20 and defining a sharply pointed tip 25 on the wire guide 20; and an aluminum body 26 which is generally arcuate about a predetermined point 28 defined by the assembly 10 and has a cross sectional area that is elongate in a radial direction from the predetermined point 28. The elongate cross section is generally rectangular as illustrated, but could alternately have rounded edges or be generally oval so that it is more comfortable to handle. The body 26 has a first end portion 30 with a through bore 32 adapted to closely receive the wire guide 20 for longitudinal sliding motion with the axis of the wire guide 20 aligned with the predetermined point 28, and has a second end portion 34 having a plurality of sockets 36 extending through the body 26. Each of the sockets 36 has a portion at its end adjacent the predetermined point 28 adapted to closely receive the lug 18 and thereby precisely orient the target end 14 at the predetermined point 28, and has a portion extending through the body 20 adapted to receive the threaded end portion 16 with a part of the threaded end portion 16 accessible from the side of the body 26 opposite the predetermined point 28. A knurled cylindrical attaching member or nut 38 is adapted to engage the part of the threaded end portion 16 on the side of the body 26 opposite the predetermined point 28 when the probe 12 is engaged in one of the sockets 36 to securely hold the lug 18 and adjacent part of the threaded end portion 16 fully within the socket 36 with its target end 14 at the predetermined point 28. The four sockets 36 illustrated are aligned to provide various angles between the axes of the wire guide 20 and probe 12, for example 75, 90, 105 and 120 degrees respectively. A body having sockets that provide these angles has been found useful for most procedures in which a wire guide assembly is needed. While the second end portion 34 of the body 26 could be extended to provide sockets 36 that afford even larger angles between the wire guide 20 and probe 12, it has been found from experience with prior art wire guide assemblies that afford such larger angles that the increased length of the body needed to afford such angles can interfere with many procedures in which the wire guide and probe are set at the lesser angles.

Holding means in the form of a U-shaped spring 40 made from flat metal spring stock is provided for preventing movement of the wire guide 20 away from the predetermined point 28 unless the holding means is manually released, while affording movement of the wire guide 20 toward the predetermined point through the bore 32 without manual manipulating the holding means. The U-shaped spring 40 has one generally straight portion 42 attached to the body 26 as by two rivets 43 on the side of the body 26 opposite the predetermined point 28, a generally straight cantilevered portion 44 connected to the attached portion 42 by a U-shaped portion and positioned on the side of the attached portion 42 opposite the body 26, and openings 46 and 47 through the attached and cantilevered portions 42 and 44 of the spring 40, respectively, which openings 46 and 47 are both generally aligned with the bore 32 and of sufficient diameter to afford longitudinal sliding movement of the wire guide 20 through the openings 46 and 47 and the bore 32 when the cantilevered portion 44 of the spring is manually deflected toward the body 26 to position the cantilevered straight portion 44 generally parallel to the attached straight portion 42. When the opening 47 moves out of alignment with the bore 32 as the cantilevered portion 44 of the spring 40 moves to its normal position, the edges of the cantilevered portion 44 defining the opening 47 engage the wire guide 20 and prevent its movement away from the predetermined point 28. When the wire guide 20 is pushed (manually or otherwise) toward the predetermined point 28, however, the cantilevered portion 44 of the spring 40 moves with it toward a position parallel with the attached portion 42 so that the wire guide 20 can move through the openings 46 and 47 and the bore 32.

The arcuate end of the U-shaped spring 40 and the first end portion 30 of the body 26 have slots 50 and 52 into the openings 46 and 47 and bore 32, respectively which afford removal of the drill guide assembly 10 from around a wire inserted into a bone after the wire guide 20 has been removed from over the wire as will be more thoroughly explained hereinafter.

The wire guide 20 has marks along its length (e.g., every centimeter and consecutively numbered from a "0" mark 54 toward the end surface 24) indicating by the location of the marks relative to the side of the body 26 adjacent the predetermined point 28, the distance between the contact end surface 24 of the drill guide 20 and the predetermined point 28. Thus the marks allow the surgeon to determine the length of wire that will be inserted between the wire guide 20 and target end 14, and thereby the length of the passageway that will be bored in the bone around the wire.

Figure 4:
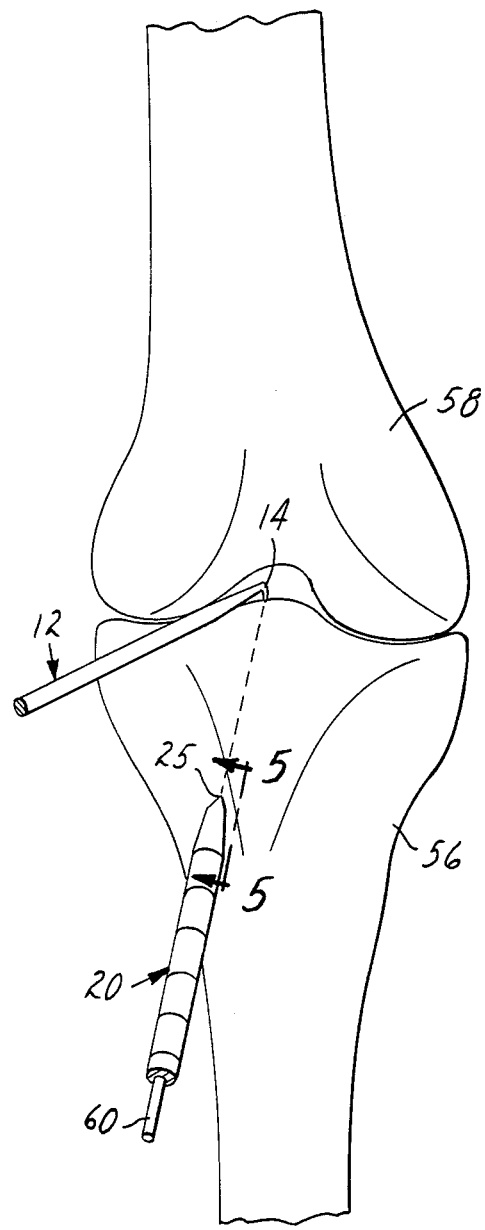
FIG. 4 is a fragmentary view of the drill guide assembly of FIG. 1 engaged with a portion of bone as a wire is inserted.
Figure 5:
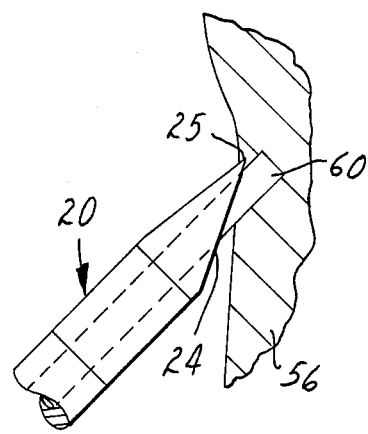
FIG. 5 is an enlarged fragmentary sectional view, taken approximately along line 5—5 of FIG. 4.

To use the drill guide assembly 10 a user first inserts the threaded end portion 16 of the probe 12 in the socket 36 that provides the desired angle between the probe 12 and the wire guide 20 to accommodate the shape of a bone portion through which the wire is to be inserted, and then engages and tightens the knurled nut 38 on the end of the threaded portion 16 to securely engage the locating lug 18 on the probe 12 in the socket 36 so that its target end 14 will be precisely positioned at the predetermined point 28. The probe 12 is then positioned with its target end 14 at a location on the bone (e.g., such as on a tibia 56 in a knee joint adjacent a femur 58 as is illustrated in FIG. 4) at which the leading end of the wire to be inserted is desired to be located, typically by inserting the probe 12 through an incision, and the wire guide 20 is pressed through the openings 46 and 47 in the spring 40 and the bore 32 in the body 26 to bring its beveled contact end surface 24 to a location along the bone at which the wire is to be inserted, also typically through an incision. As is best seen in FIG. 5, the contact end surface 24 is positioned so that it forms a minimum included angle with the surface of the bone, and the wire guide 20 is impacted on its end opposite its tip 25 (as with a hammer) to drive the tip 25 into the bone to stabilize its position relative to the bone and to further decrease the distance between the end surface 24 and the bone. The user can then determine the distance through the bone between the end surface 24 of the wire guide 20 and the target end 14 by reading the marks on the wire guide 20 at the side of the body 26 adjacent the probe 12, which may be helpful during the balance of the operation. A wire 60 is then inserted into the bone through the wire guide 20 until it reaches the target end 14 of the probe 12, and the drill guide assembly 10 is removed from the inserted wire by manually compressing the cantilevered part 44 of the spring 40 and pulling the wire guide 20 from the bore 32 and openings 46 and 47 in the compressed spring 40 over the end of the wire 60. The body 26 is then moved from over the wire 60 by moving it in the plane of the body so that the walls defining the slots 52 and 50 in the body 26 and spring 40 pass over the wire 60, and the probe 12 is removed from the incision. The use of the drill guide assembly 10 is then complete, and the user can drill an accurately positioned opening in the bone using a cannulated drill guided by the inserted wire 60.

The present invention has now been described with reference to one embodiment thereof. It will be apparent to those skilled in the art that many changes can be made in the embodiment described without departing from the scope of the present invention, as for example, by using some of the novel features hereof without using others. Thus the scope of the present invention should not be limited to the structures described in this application, but only by structures described by the language of the claims and the equivalents of those structures.

We claim:

1. A drill guide assembly for use in arthroscopic surgery, said drill guide assembly comprising:
   a probe having a target end, an opposite threaded end portion and a locating lug at the end of said threads adjacent said target end;
   a cannular elongate cylindrical wire guide having a central through opening adapted to receive and guide a guide wire, said wire guide having an entirely planar beveled end surface disposed at an angle of about 25 degrees with respect to the axis of said wire guide;
   a body generally arcuate about a predetermined point and having a cross sectional area that is elongate in a radial direction from said predetermined point, having a first end portion with a through bore adapted to closely receive said wire guide for longitudinal sliding action with the axis of said wire guide aligned with said predetermined point, and having a second end portion having a plurality of sockets extending through said body, each socket adapted to receive said lug and threaded end portion with said target end at said predetermined point and a part of said threaded end portion accessible from the side of said body opposite said predetermined point;

an attaching member adapted to engage the part of said threaded end portion on the side of said body opposite said predetermined point when said probe is engaged in one of said sockets; and means for preventing movement of said wire guide away from said predetermined point.

2. A drill guide assembly for use in arthroscopic surgery, said drill guide assembly comprising:

a probe having a target end, an opposite threaded end portion and a locating lug at the end of said threads adjacent said target end;

a cannular elongate cylindrical wire guide having a central through opening adapted to receive and guide a guide wire;

a body generally arcuate about a predetermined point and having a cross sectional area that is elongate in a radial direction from said predetermined point, having a first end portion with a through bore adapted to closely receive said wire guide for longitudinal sliding action with the axis of said wire guide aligned with said predetermined point, and having a second end portion having a plurality of sockets extending through said body, each socket adapted to receive said lug and threaded end portion with said target end at said predetermined point and a part of said threaded end portion accessible from the side of said body opposite said predetermined point;

an attaching member adapted to engage the part of said threaded end portion on the side of said body opposite said predetermined point when said probe is engaged in one of said sockets; and means for preventing movement of said wire guide away from said predetermined point, said means for preventing movement of said wire guide away from said predetermined point comprising a U-shaped spring including one attached portion attached to said body on the side of the body opposite said predetermined point and a cantilevered portion on the side of said attached portion opposite said body, said spring having openings through said portions, which openings are both generally aligned with said bore and of sufficient diameter to afford longitudinal sliding movement of said wire guide through said openings and said bore when the cantilevered portion of the spring is deflected toward said body, which deflection will occur when the wire guide is moved toward said predetermined point, said opening in said cantilevered portion moving out of alignment with said bore when said cantilevered portion moves to its normal position so that the edges of the cantilevered portion defining the opening therein engage said wire guide to prevent movement of the wire guide away from said predetermined point.

3. A drill guide assembly for use in arthroscopic surgery, said drill guide assembly comprising:

a probe having a target end, an opposite threaded end portion and a locating lug at the end of said threads adjacent said target end;

a cannular elongate cylindrical wire guide having a central through opening adapted to receive and guide a guide wire;

a body generally arcuate about a predetermined point and having a cross sectional area generally perpendicular to the arc of the body that is elongate in a radial direction from said predetermined point, having a first end portion with a through bore adapted to closely receive said wire guide for longitudinal sliding action with the axis of said wire guide aligned with said predetermined point, and having a second end portion having a plurality of sockets extending through said body, each socket adapted to receive said lug and threaded end portion with said target end at said predetermined point and a part of said threaded end portion accessible from the side of said body opposite said predetermined point;

an attaching member adapted to engage the part of said threaded end portion on the side of said body opposite said predetermined point when said probe is engaged in one of said sockets;

means for preventing movement of said wire guide away from said predetermined point; and means for permitting moving said body and means for preventing movement from around a wire positioned through said bore after said wire guide is removed from said bore and means for preventing movement, the means for permitting moving including corresponding slots in the first end portion of the body and the means for preventing movement, the slots being adapted for affording moving the body and means for preventing movement from around a guide wire positioned through the bore after the wire guide is removed from the bore and the means for preventing movement.

4. A drill guide assembly for use in arthroscopic surgery, said drill guide assembly comprising:

a probe having a target end and an opposite end portion;

a cannular elongate cylindrical wire guide having a central through opening adapted to receive and guide a guide wire;

a body generally arcuate about a predetermined point, having a first end portion with a through bore adapted to closely receive said wire guide for longitudinal sliding action with the axis of said wire guide aligned with said predetermined point, and having a second end portion;

means adapted for engagement between said opposite end portion of the probe and said second end portion of the body to position said probe with said target end at said predetermined point;

holding means for preventing movement of said wire guide away from said predetermined point, while affording movement of said wire guide toward said predetermined point without manual manipulation of said holding means.

5. A drill guide assembly according to claim 4, wherein said wire guide has an entirely planar beveled end surface disposed at an angle of about 25 degrees with respect to the axis of said wire guide.

6. A drill guide assembly according to claim 4 wherein said holding means comprises a U-shaped spring including one attached portion attached to said body on the side of the body opposite said predetermined point and a cantilevered portion on the side of said attached portion opposite said body, and having openings through said portions, which openings are both generally aligned with said bore and of sufficient diameter to afford longitudinal sliding movement of said wire guide through said openings and said bore when the cantilevered portion of the spring is deflected toward said body, which deflection will occur when the wire guide is moved toward said predetermined point, said opening in said cantilevered portion moving out of alignment with said bore when said cantilevered portion moves to its normal position so that the edges of the cantilevered portion defining the opening therein engage said wire guide to prevent movement of the wire guide away from said predetermined point.

7. A drill guide assembly according to claim 4 further comprising means for permitting moving said body and holding means from around a wire positioned through said bore after said wire guide is removed from said bore and holding means, the means for permitting moving including corresponding slots in the first end portion of the body and the holding means, the slots being adapted to permit moving the body and holding means from around a guide wire positioned through the bore after the wire guide is removed from the bore and the holding means.

8. A drill guide assembly for use in arthroscopic surgery, said drill guide assembly comprising:
 a probe having a target end and an opposite end portion;
 a cannular elongate cylindrical wire guide having a central through opening adapted to receive and guide a guide wire, and an entirely planar beveled end surface;
 a body generally arcuate about a predetermined point, having a first end portion with a through bore adapted to closely receive said wire guide for longitudinal sliding action with the axis of said wire guide aligned with said predetermined point, and having a second end portion;
 means adapted for engagement between said opposite end portion of the probe and said second end portion of the body to position said probe with said target end at said predetermined point;
 holding means for preventing movement of said wire guide away from said predetermined point.

9. A drill guide assembly according to claim 8, wherein said beveled end surface is disposed at an angle of about 25 degrees with respect to the axis of said wire guide.

10. A drill guide assembly according to claim 8 further comprising means for permitting movement of said body and holding means from around a wire positioned through said bore after said wire guide is removed from said bore and holding means, the means for permitting movement including corresponding slots in the first end portion of the body and the holding means, the slots being adapted to permit moving the body and holding means from around a guide wire positioned through the bore after the wire guide is removed from the bore and the holding means.

* * * * *